United States Patent
Brown et al.

(10) Patent No.: US 11,253,318 B2
(45) Date of Patent: Feb. 22, 2022

(54) ARRANGEMENT FOR FILTERING OUT DAMAGING HEAT CREATED FROM LASER ENERGY CONTACTING A KIDNEY STONE

(71) Applicant: Optical Integrity, Inc., Panama City Beach, FL (US)

(72) Inventors: Joe Denton Brown, Panama City Beach, FL (US); Daniel Malphurs, Panama City Beach, FL (US)

(73) Assignee: OPTICAL INTEGRITY, INC., Panama City Beach, FL (US)

( * ) Notice: Subject to any disclaimer, the term of this patent is extended or adjusted under 35 U.S.C. 154(b) by 47 days.

(21) Appl. No.: 16/527,359

(22) Filed: Jul. 31, 2019

(65) Prior Publication Data

US 2020/0060764 A1    Feb. 27, 2020

Related U.S. Application Data

(60) Provisional application No. 62/720,365, filed on Aug. 21, 2018.

(51) Int. Cl.
| | | |
|---|---|---|
| *A61B 18/20* | (2006.01) | |
| *A61B 18/24* | (2006.01) | |
| *A61B 18/26* | (2006.01) | |
| *A61B 18/22* | (2006.01) | |

(52) U.S. Cl.
CPC ............ *A61B 18/245* (2013.01); *A61B 18/26* (2013.01); *A61B 2018/2015* (2013.01); *A61B 2018/2244* (2013.01)

(58) Field of Classification Search
CPC .................. A61B 18/245; A61B 18/26; A61B 2018/2015; A61B 2018/2244
See application file for complete search history.

(56) References Cited

U.S. PATENT DOCUMENTS

| | | | | |
|---|---|---|---|---|
| 5,638,483 A | * | 6/1997 | Konwitz | A61B 18/24 362/553 |
| 6,282,349 B1 | | 8/2001 | Griffin | |
| 7,273,478 B2 | | 9/2007 | Appling et al. | |
| 2003/0219202 A1 | * | 11/2003 | Loeb | A61B 18/245 385/33 |
| 2008/0188843 A1 | * | 8/2008 | Appling | A61B 18/24 606/15 |

(Continued)

FOREIGN PATENT DOCUMENTS

| | | | | |
|---|---|---|---|---|
| WO | WO-2017192869 A1 | * | 11/2017 | ............ A61B 18/22 |
| WO | WO2017192869 A1 | | 11/2017 | |

*Primary Examiner* — Allen Porter
*Assistant Examiner* — Skylar Lindsey Christianson
(74) *Attorney, Agent, or Firm* — Bacon & Thomas, PLLC

(57) ABSTRACT

An arrangement that prevents carbonization of cladding, coating, or buffer layers of a surgical laser fiber due to thermal radiation reflected back into the fiber from, or emitted by, a target of the laser, includes a thermal radiation blocking, absorbing or diverting structure. The thermal radiation blocking, absorbing or diverting structure surrounds an end portion of the fiber that has been stripped of one or more coating and/or buffer layers, and may be made of a heat resistant material such as PTFE or polyimide to block heat from reaching the coating or buffer layers, an optical ferrule such as fused silica to guide the heat away from the fiber coating or buffer layers, or a high refraction index material such as UV adhesive.

19 Claims, 9 Drawing Sheets

(56) References Cited

U.S. PATENT DOCUMENTS

| | | | | |
|---|---|---|---|---|
| 2015/0282701 A1* | 10/2015 | Oskin | ................ | A61B 1/00066 |
| | | | | 600/131 |
| 2017/0135767 A1* | 5/2017 | Zerfas | .................... | A61B 18/26 |
| 2018/0021088 A1* | 1/2018 | Scheller | ................ | A61B 18/22 |
| | | | | 606/4 |
| 2018/0042677 A1* | 2/2018 | Yu | .......................... | A61B 18/22 |

* cited by examiner

ARRANGEMENT FOR FILTERING OUT DAMAGING HEAT CREATED FROM LASER ENERGY CONTACTING A KIDNEY STONE

This application claims the benefit of U.S. Provisional Patent Appl. Ser. No. 62/720,365, filed Aug. 21, 2019.

BACKGROUND OF THE INVENTION

1. Field of the Invention

The invention relates to an arrangement for preventing damage to an optical fiber caused by thermal radiation reflected back into the fiber from a surgical laser target such as a kidney stone.

More particularly, the invention provides a structure that prevents reflected thermal radiation from carbonizing layers of the fiber by blocking, absorbing and/or diverting the reflected thermal radiation. The carbonization preventing structure surrounds the fiber core and cladding at the distal end of the fiber, replacing coating and/or buffer layers that have been stripped from the fiber, to form a filter for the reflected thermal radiation.

The carbonization preventing structure may advantageously be combined with a surrounding standoff or protective tip structure that establishes a minimum spacing between the surgical laser target and the tip of the fiber, in order to prevent or limit erosion of the fiber tip due to free electron erosion.

2. Description of Related Art

FIG. 1 shows an example of a conventional laser fiber for lithotripsy procedures that utilize a laser to destroy a kidney stone that has become lodged in the urinary tract of a patient. The exemplary laser fiber includes a fused silica core 1, a fluorine doped fused silica cladding layer 2, a hard polymer coating layer 3, and an ethylene tetrafluoroethylene (ETFE) buffer layer 4. The fiber may be further enclosed within an outer jacket, but the end of the fiber is typically stripped of the jacket and therefore the jacket is not shown in FIG. 1. In order to confine the laser energy to the core 1 of the fiber, the index of refraction (RI) of the cladding layer 2 is higher than that of the core. For the illustrated fiber, exemplary indices of refraction (RI) of the respective layers for a laser wavelength of 1064 nm are: RI=1.4571 for the core 1; RI=1.440 for the cladding layer 2; RI=1.395 for the hard polymer coating layer 3; and RI=1.4 for the ETFE buffer layer 4. It will be appreciated by those skilled in the art that the exemplary materials, refraction indices, and laser wavelength are typical but not intended to be limiting, and that the materials, refraction indices, and laser wavelength have been and may be varied for lithotripsy and other surgical applications.

During a surgical procedure, as shown in FIG. 2, the fiber is inserted through an introducer or endoscope until the end of the fiber faces a stone 6 to be destroyed. When laser energy is directed at the stone 6, thermal radiation represented by arrows 9 is generated and passes back into the fiber. The thermal radiation is not confined to the core 1 and cladding layer 2, but instead also enters coating and buffer layers 3 and 4, which have a relatively low operating temperature compared to the silica core and silica cladding layers, and therefore are vulnerable to charring that forms carbonization zones 5 at different spots along the fiber axis. When a carbonization zone 5 touches the silica cladding layer 2, the fiber becomes very weak and can easily break when bent.

In addition, as the bare fiber of FIG. 2 approaches or contact the stone 6, the thermal radiation entering the fiber becomes sufficient to create free electron absorption (FEA) or fiber fusing, resulting in erosion of the distal tip of the fiber, indicated in FIG. 3 by reference number 11. Erosion can be prevented by adding a polymer or metal spacer or standoff sleeve that extends beyond the distal end of the fiber to provide a predetermined spacing or standoff between the fiber and the stone 6 or other surgical laser target, as shown in FIG. 4. Examples of spacers or sleeves are disclosed in copending PCT Appl. Ser. No. PCT/US2017/031091 (PCT Publ. No. WO/2017/192869), filed May 4, 2017, which is incorporated by reference herein. By ensuring a minimum spacing between the fiber tip and the stone, use of the spacer or standoff sleeve prevents fiber erosion and limits carbonization to a predictable area. In addition, if the spacer or standoff sleeve is made of metal and securely fastened to the fiber buffer, for example by crimping, the spacer or sleeve can provide additional structural support to prevent breakage of the fiber due to carbonization.

The present invention provides added protection against effects of carbonization, and in addition can be used with or without a spacer tip or standoff sleeve, by blocking, absorbing or deflecting thermal radiation away from fiber layers vulnerable to carbonization.

SUMMARY OF THE INVENTION

It is accordingly an objective of the invention to provide an arrangement that prevents carbonization of cladding, coating, or buffer layers of a surgical laser fiber due to passage of thermal radiation from a target of the laser, such as by way of example and not limitation, a kidney stone lodged in the urinary tract of a patient.

In a first preferred embodiment of the invention, the carbonization preventing arrangement consists of a heat or thermal radiation blocking, absorbing or diverting structure that surrounds an end portion of the fiber that has been stripped of one or more coating and/or buffer layers.

The heat or thermal radiation blocking, absorbing or diverting structure may, by way of example and not limitation, be made of a heat resistant material such as polyetheretherketone (PEEK), polyethylene terephthalate (PTFE) or polyimide to block, absorb, and/or dissipate thermal radiation before it reaches the coating or buffer layers.

In alternative embodiments of the invention, the carbonization preventing structure may take the form of a fused silica ferrule or high index of refraction structure made of a material such as a UV adhesive to guide the thermal radiation toward a heat sink and/or away from the fiber coating or buffer layers.

Optionally, the end of the fiber, including at least the heat blocking, absorbing or diverting structure, may be surrounded by an additional standoff or fiber tip protective structure. The standoff or fiber trip protective structure may be a soft polymer tip made of a material such as PTFE or ETFE, as described in copending PCT Appl. Ser. No. PCT/US2017/031091, or a rigid ferrule made of a material such as fluorinated ethylene propylene (FEP), PEEK, metal, fused silica, quartz, polyimide, or ceramic, including structures of the type disclosed in U.S. Pat. Nos. 7,273,478 and 6,282,349, U.S. Patent Publication No. 2008/0188843, and provisional U.S. Patent Appl. Ser. No. 60/395,218.

The distal end of the optional standoff or fiber tip protective structure may be flush with or extend beyond the distal end of the fiber, or the distal end of the fiber may extend beyond the fiber tip. If the protective structure does not extend beyond the end of the fiber, erosion may occur as a result of contact with the stone, but the erosion is limited because the protective structure will prevent further erosion once the fiber tip is no longer able to contact the stone. Erosion can be completely prevented by extending the protective structure beyond the end of the fiber, but the increased spacing between the fiber and the stone will have the effect of lowering the density of power applied to the stone.

Instead of a standoff or fiber tip protective structure that only covers and is attached to the end of the fiber, the standoff or protective structure may take the form of, or be fixed to, a catheter or sheath into which the fiber, modified to prevent carbonization, has been inserted.

DETAILED DESCRIPTION OF THE PREFERRED EMBODIMENTS

Figure 1:
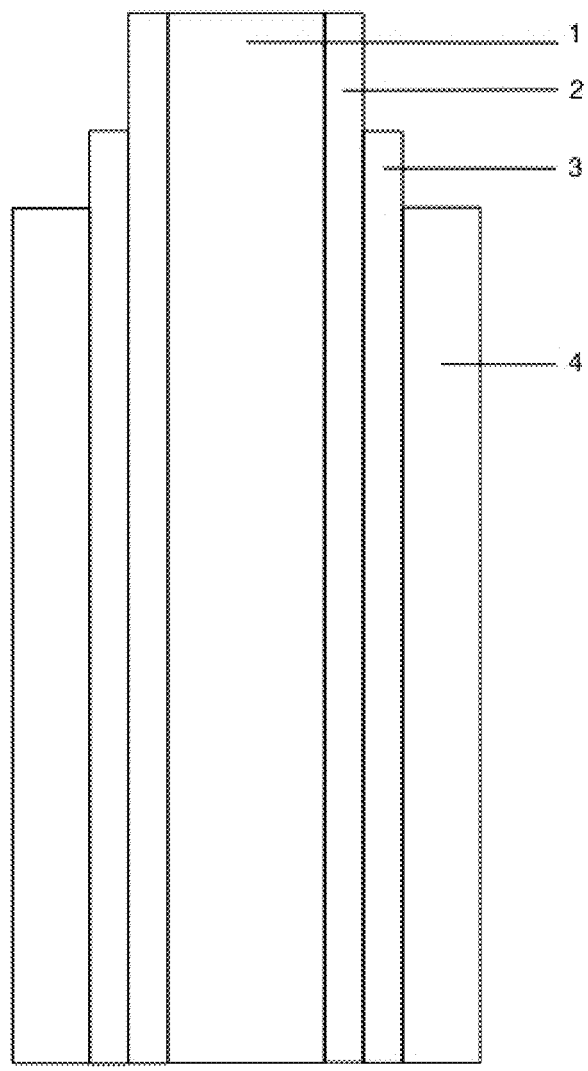
FIG. 1 is a cross-sectional side view of a conventional surgical laser fiber to which the principles of the present invention may be applied.
Figure 2:
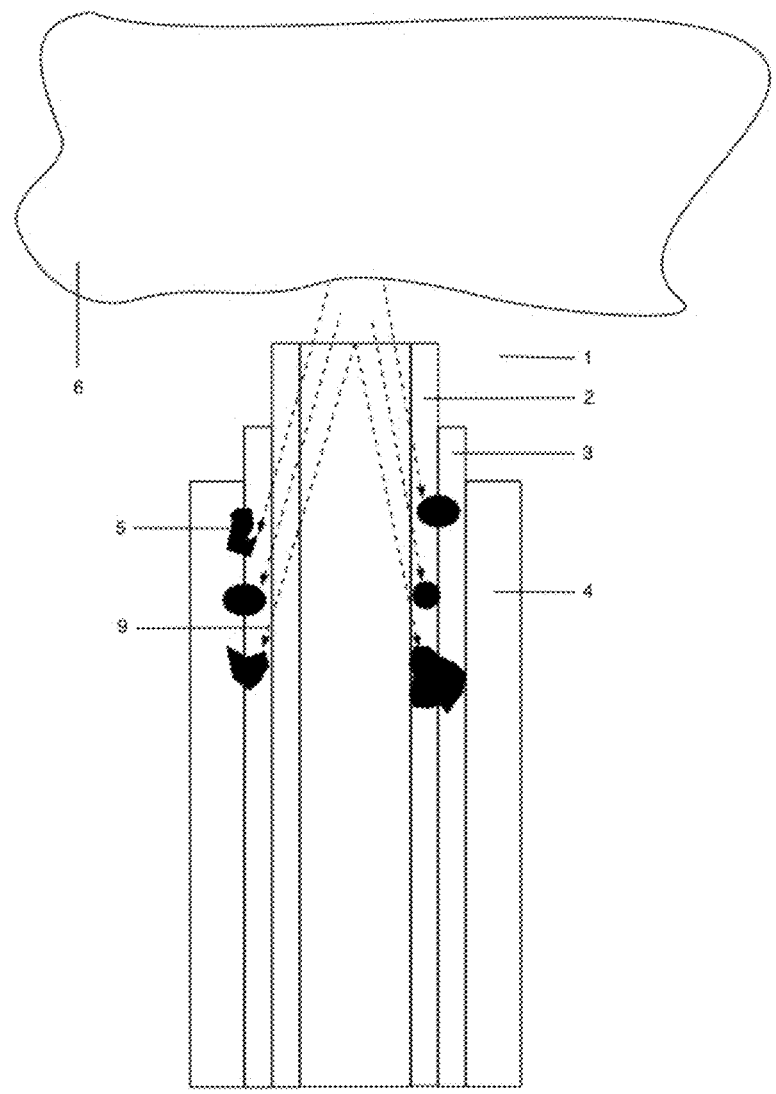
FIG. 2 is a cross-sectional side view showing the effects of thermal radiation reflection from a stone on the conventional fiber of FIG. 1.
Figure 3:
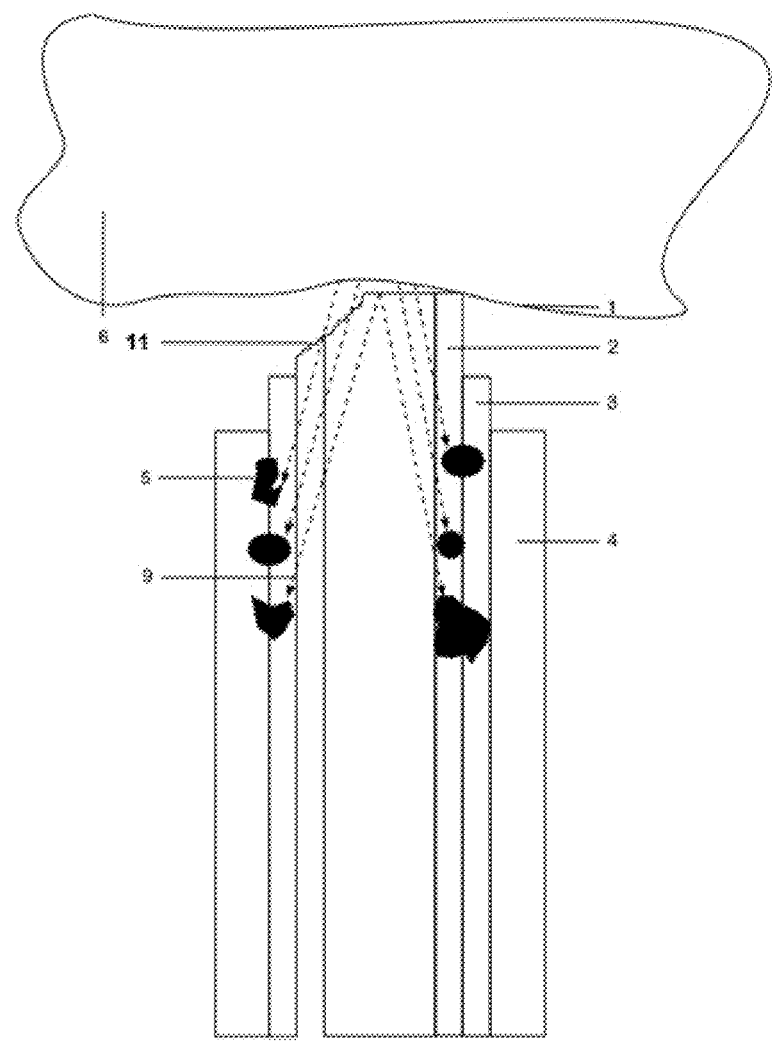
FIG. 3 is a cross-sectional side view showing erosion effects of free electron absorption when the conventional fiber of FIG. 1 contacts the stone during a lithotripsy procedure.
Figure 5:
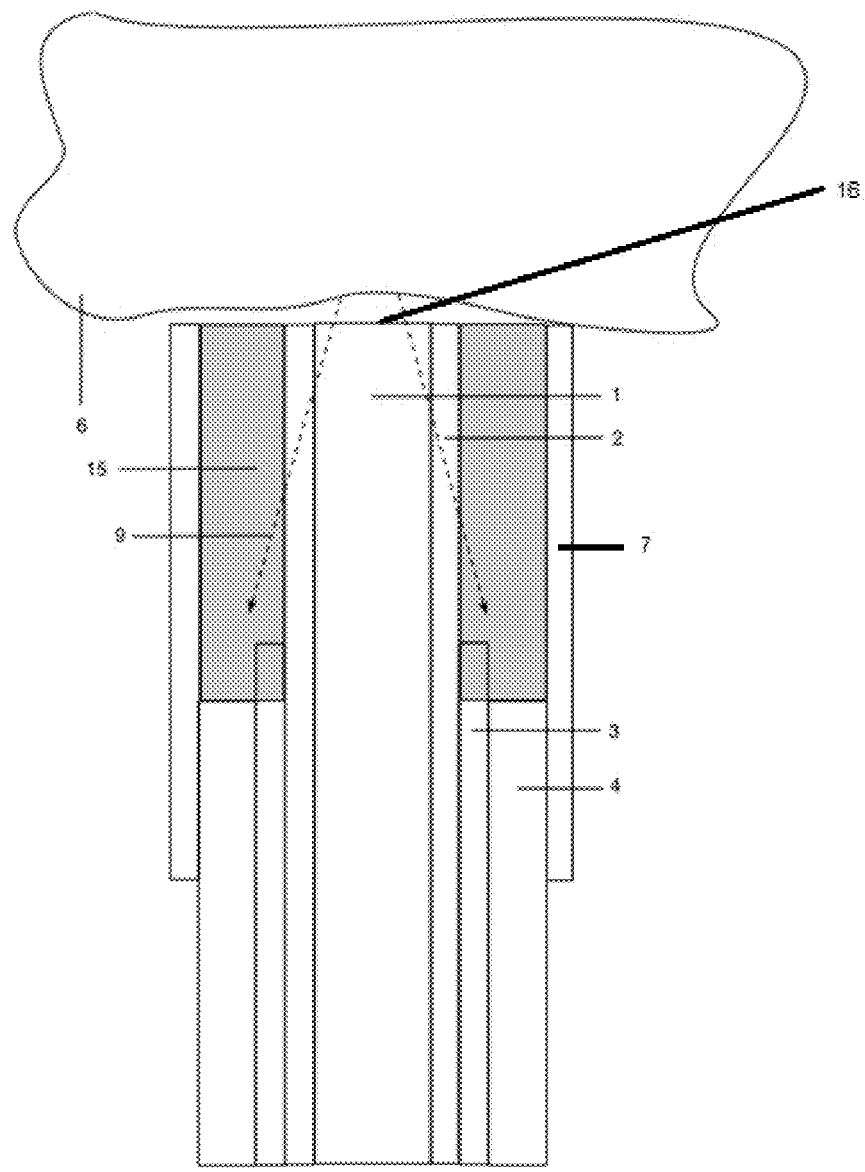
FIG. 5 is a cross-sectional side view of a surgical fiber laser fiber that has been modified to prevent carbonization in accordance with the principles of a first preferred embodiment of the invention.

FIG. 5 shows a carbonization preventing arrangement according to a first preferred embodiment of the invention. The carbonization preventing arrangement is applied, for illustrative purposes, to a surgical laser fiber such as the one shown in FIG. 1, which includes a fused silica core 1, a fluorine doped fused silica cladding layer 2, a hard polymer coating layer 3, and an ethylene tetrafluoroethylene (ETFE) buffer layer 4. The materials and configuration of the core and fiber layers are exemplary and may be varied without departing from the scope of the present invention. In addition, the illustrations of the fiber are schematic in nature, and not intended to provide an indication of scale.

The carbonization preventing arrangement of FIG. 5 is implemented by replacing a section of the coating layer 4 and buffer layer 5 with a thermal radiation blocking, absorbing and/or redirecting structure 15 that extends towards the distal end of the fiber, and that prevents damage to the fiber by blocking, absorbing and/or redirecting thermal radiation away from the coating layer 4 or buffer layer 5.

Suitable materials for the carbonization preventing structure 15 include a heat resistant material such as polyimide that prevents thermal radiation from passing between the end of the fiber and the coating layer 4 or buffer layer 5, a heat conductive material such as a silica ferrule welded to the cladding and connected to a heat sink to dissipate or conduct the thermal radiation away from the coating layer 4 or buffer layer 5, or a high index of refraction material such as a UV adhesive. Optionally, a surface of the carbonization prevention structure 15 may be roughened to provide an enlarged surface area for heat dissipation.

Figure 4:
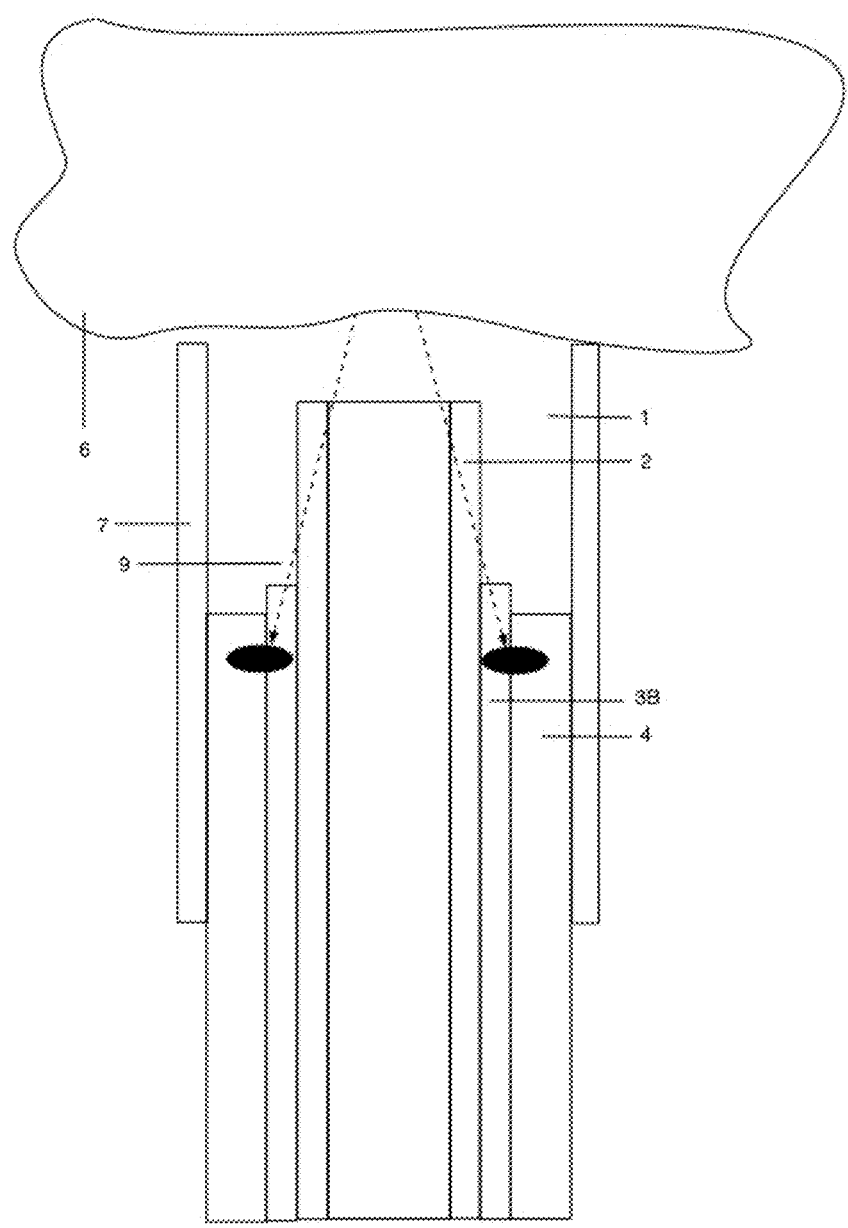
FIG. 4 is a cross-sectional side view showing effects of adding a stand-off tip or protective sleeve to the end of the conventional fiber.

As shown in FIG. 5, the carbonization preventing structure 15 is flush with the distal end 16 of the fiber and may be surrounded by the standoff tip or protective sleeve 7 illustrated in FIG. 4. This arrangement maximizes the power density that reaches the stone 6 during lasing. While some erosion will occur, the erosion is effectively controlled and will stop when the distal end 16 of the fiber no longer contacts the stone, creating a set back of the distal end 16 of the fiber with respect to the end surface of the standoff tip that prevents surgical laser target from contacting the fiber.

Figure 6:
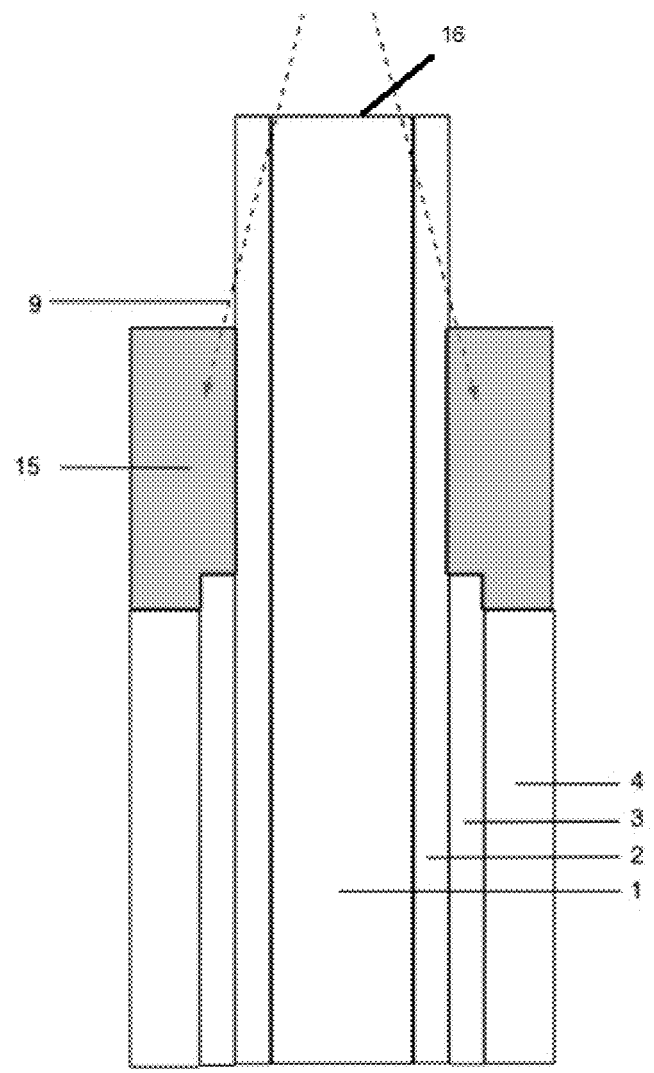
FIG. 6 is a cross-sectional side view of a variation of the carbonization prevention arrangement of FIG. 5, in which the carbonization-preventing thermal radiation blocking, absorbing, or diverting material that prevents thermal radiation from entering cladding, coating or buffer layers of the fiber is set back from the fiber tip.

Alternatively, as shown in FIG. 6, the standoff may be omitted and the carbonization preventing structure 15 set back from the tip of the fiber. Such a stand-off free arrangement also maximizes power density while protecting the coating or buffer layers 4 and 5 from thermal radiation, but does not prevent erosion of the fiber due to contact with a surgical laser target or stone. This alternative is especially suitable for short pulse lasers, since the short pulses do not provide time for free electron absorption to occur, and therefore are not as vulnerable to erosion of the fiber tip.

Figure 7:
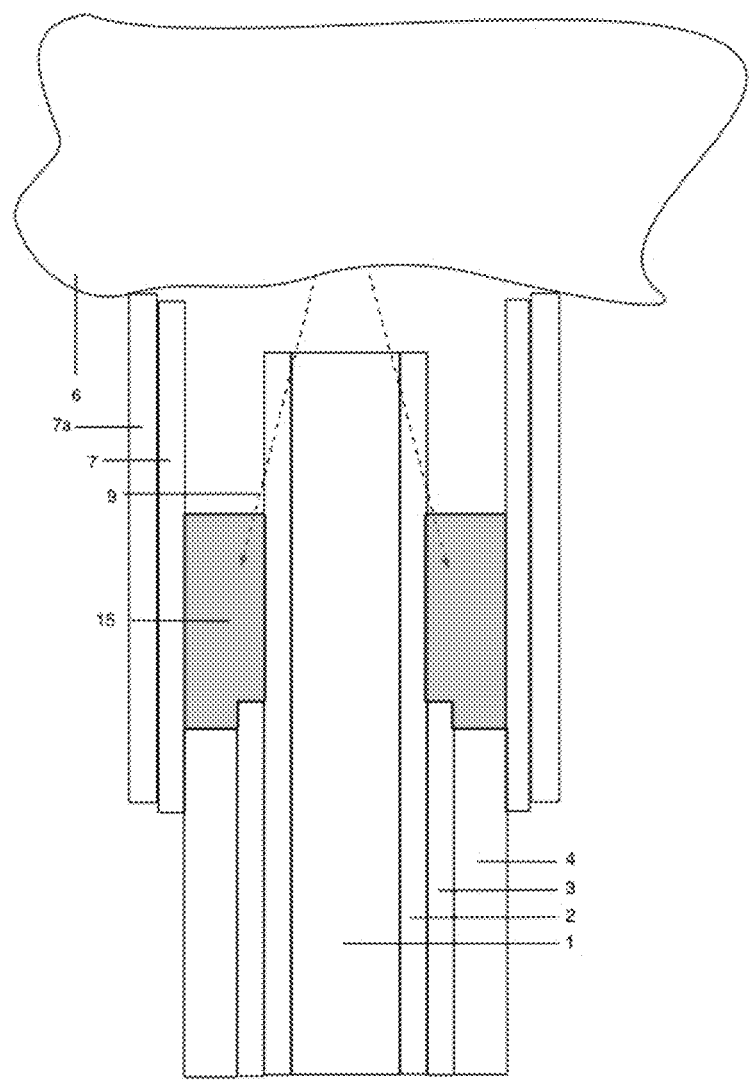
FIG. 7 is a cross-sectional side view showing a variation of the carbonization preventing arrangement of FIG. 6, in which a standoff tip or sleeve of the type illustrated in FIG. 4 is added.

As shown in FIG. 7, the carbonization prevent structure 15 is set back and in FIG. 6, but a standoff or protective sleeve 7 is provided. In this variation of the embodiment of FIG. 5, the standoff or protective sleeve 7 extends beyond the end of the fiber, so as to prevent any fiber erosion from occurring while reducing the amount of laser energy that reaches the target or stone. Alternatively, the fiber tip may extend beyond the end of standoff or protective sleeve 7, which allows for more erosion as in the variation of FIG. 5, but with a higher power density. If the standoff or protective sleeve 7 is made of a hard material such as ceramic, glass or metal, then an optional soft layer 7a may be added to protect the endoscope and tissue. Optional soft layer 7a may be made of a material such as ETFE, PTFE, silicone, or other relatively soft or flexible materials.

As noted above, the standoff tip or protective sleeve may be made of a relatively rigid material such as PEEK, PTFE, FEP, metal, fused silica, quartz, polyimide, and ceramic, or a relatively soft polymer material ETFE. The softer material has the advantage of protecting the interior of the scope during insertion. A similar scope-protecting effect can be achieved by providing the standoff with rounded edges. Although not shown, the standoff tip or protective sleeve may alternatively be part of a catheter or sheath that extends the length of the fiber, or through which the fiber is inserted, rather than being limited to and/or fixed to the distal end of the fiber.

Figure 8:
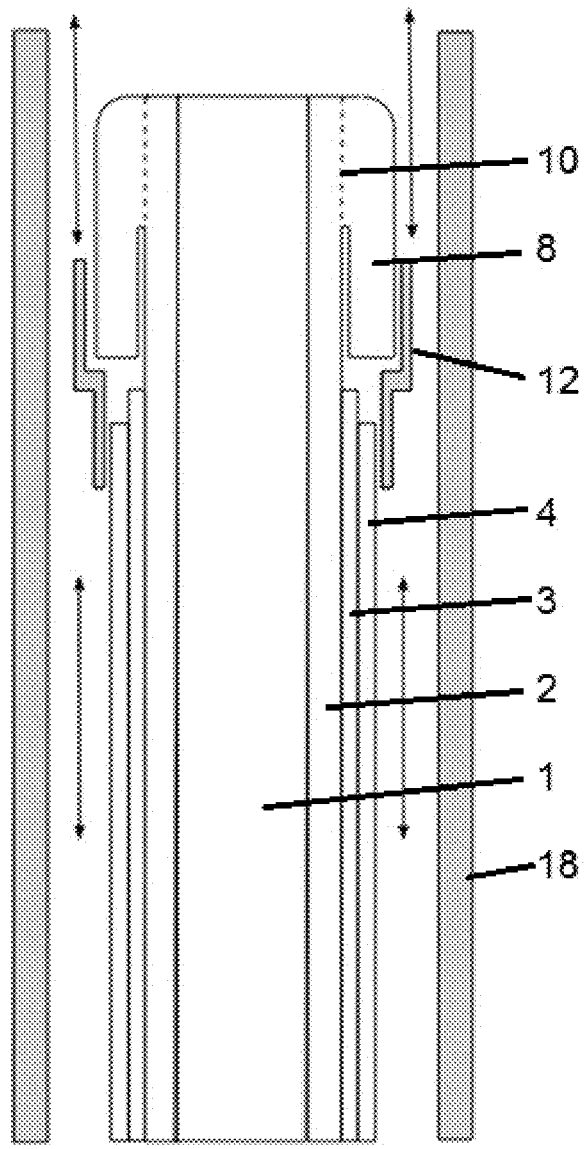
FIG. 8 is a cross-sectional side view of a surgical laser fiber that has been modified to prevent carbonization in accordance with the principles of a second preferred embodiment of the invention.

FIG. 8 shows an alternative embodiment in which the carbonization preventing structure is a silica ferrule 8 that has been welded to the fiber cladding layer 2 along weld line 10. An optional metal heat sink 12 in thermal contact with the ferrule 8 may be added and secured to the buffer layer 4 of the fiber by crimping or gluing. The silica ferrule 8 can itself serve as a standoff to prevent fiber erosion, although a standoff of the type disclosed in FIGS. 4, 5, and 7 may be added.

In the embodiment shown in FIG. 8, the standoff or protective tip of FIGS. 4, 5, and 7 is replaced by a catheter or sheath 18 in to which the fiber has been inserted, and which can serve as a standoff to prevent contact between the laser target and the fiber. The same catheter or sheath can be used in connection with the carbonization prevention arrangement shown in any of FIGS. 4-7.

Figure 9:
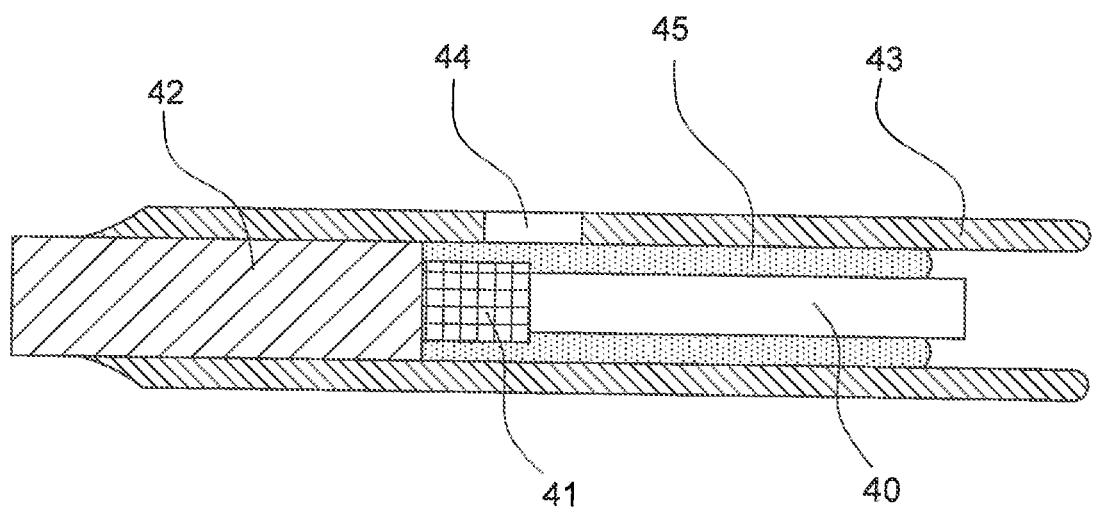
FIG. 9 is a cross-sectional side view of a surgical laser fiber that has been modified to prevent carbonization in accordance with the principles of a third preferred embodiment of the invention.

In the embodiment of FIG. 9, a silica clad fiber 40 with polymer cladding layer 41 and polymer buffer layer 42 is protected by a polymer standoff jacket 43. As in the embodiment of FIGS. 5-7, radiation that travels back into the fiber 40 after it is reflected from or emitted by a target is blocked, absorbed, or diverted by a carbonization preventing structure 45.

In order to improve the temperature tolerance of the fiber's distal termination and prevent carbonization, the fiber 40 is stripped down to the silica cladding by removing the polymer coatings 41 and 42. However, in this embodiment, the fiber 40 is still surrounded by or, in some cases, recessed in the standoff jacket 43.

The carbonization structure of this embodiment is in the form of a polymer 45 that fills the space between the outer diameter of the fiber 40 and the inner diameter of the standoff jacket 43. The polymer 45 is more optically dense than the fiber cladding and has a high heat tolerance so that the polymer 45 can absorb and/or disperse the back-fed energy that would normally damage the polymer coatings 41 and 42.

By using a flexible material for polymer 45, and/or standoff jacket 43, the fiber distal end assembly can withstand substantial shock from handling and from the shockwaves produces by laser treatment in the treatment area. Another benefit of using flexible polymers is that the tip is less traumatic to tissue and other surgical equipment. Finally, yet another benefit in using flexible polymers for 45 and 43 is that the fiber tip assembly can achieve a tighter bend radius by bending and conforming to the endoscope's working channel.

What is claimed is:

1. An arrangement for preventing carbonization of cladding, coating, and/or buffer layers of a surgical laser fiber due to reflection of thermal radiation back into the fiber from a target, the reflection of thermal radiation resulting from delivery of laser energy from a laser to the target through the surgical laser fiber, and the surgical laser fiber including a core surrounded by said cladding, coating or buffer layers, comprising:
   a heat or thermal radiation blocking, absorbing or diverting structure surrounding an end portion of the fiber that has been stripped of one or more of the coating and/or buffer layers,
   wherein the heat or thermal radiation blocking, absorbing or diverting structure replaces the coating and/or buffer layers that have stripped from the end portion of the fiber,
   wherein the heat or thermal radiation blocking, absorbing or diverting structure surrounds the end portion of the fiber to prevent back-propagation of the reflected thermal radiation through the cladding, coating or buffer layers of the fiber,
   wherein the heat or thermal radiation blocking, absorbing or diverting structure is positioned on the cladding layer between a distal end of the coating and/or buffer layers and a distal end of the fiber, and
   wherein the heat or thermal radiation blocking, absorbing or diverting structure is:
      (a) made of a heat resistant material and configured to prevent thermal radiation from passing between the end of the fiber and coating and/or buffer layers that have not been stripped from the fiber,
      (b) made of a heat conductive material fixed to the cladding layer and connected to a heat sink to dissipate or conduct the thermal radiation away from the coating and/or buffer layers that have not been stripped from the fiber, or
      (c) made of a high index of refraction material to divert thermal radiation away from the coating and/or buffer layers that have not been stripped from the fiber.

2. An arrangement as claimed in claim 1, wherein the heat and thermal radiation blocking, absorbing or diverting structure is made of a heat resistant material.

3. An arrangement as claimed in claim 2, wherein the heat resistant material is polyethylene terephthalate (PTFE), polyetheretherketone (PEEK), or polyimide.

4. An arrangement as claimed in claim 1, wherein the heat and thermal radiation blocking, absorbing or diverting structure is an optical ferrule to guide the heat away from the fiber coating or buffer layers.

5. An arrangement as claimed in claim 4, wherein the optical ferrule is made of fused silica that is welded to the cladding layer at the end of the fiber.

6. An arrangement as claimed in claim 5, further comprising a metal heat sink in thermal contact with the optical ferrule and secured to the buffer layer of the fiber by gluing or crimping.

7. An arrangement as claimed in claim 1, wherein the heat blocking, absorbing or diverting structure is made of material with a high index of refraction to guide heat away from the fiber coating and/or buffer layers.

8. An arrangement as claimed in claim 7, wherein the material with a high index of refraction is a UV adhesive.

9. An arrangement as claimed in claim 1, further comprising a standoff or fiber tip protective structure surrounding at least the heat and thermal radiation blocking, absorbing, or diverting structure.

10. An arrangement as claimed in claim 9, wherein the standoff or fiber tip protective structure is a soft polymer tip.

11. An arrangement as claimed in claim 10, wherein the soft polymer tip is made of ethylene tetrafluoroethylene (ETFE).

12. An arrangement as claimed in claim 9, wherein the standoff or fiber tip protective structure is a polyethylene terephthalate (PTFE), fluorinated ethylene propylene (FEP), polyetheretherketone (PEEK), metal, fused silica, quartz, polyimide, or ceramic ferrule.

13. An arrangement as claimed in claim 9, wherein the standoff or fiber tip protective structure includes a rigid material surrounded by an added soft material.

14. An arrangement as claimed in claim 13, wherein the rigid material is a ceramic, glass, or metal material, and the soft material is ETFE, PTFE, or silicone.

15. An arrangement as claimed in claim 9, wherein the standoff or fiber tip protective structure does not extend beyond the tip of the surgical laser fiber, such that the tip of the surgical laser fiber initially contacts the target and erodes, and wherein the erosion stops when the standoff or fiber tip extends beyond an eroded fiber tip and the surgical laser fiber no longer contacts the target.

16. An arrangement as claimed in claim 9, wherein the standoff or fiber tip protective structure extends beyond a tip of the fiber to prevent contact between the fiber tip and the target, and thereby prevent erosion-causing free-electron absorption.

17. An arrangement as claimed in claim 9, wherein the standoff or fiber tip protective structure is secured to the buffer layer near an end of the fiber.

18. An arrangement as claimed in claim 9, wherein the standoff or fiber tip protective structure is a catheter or sheath into which the fiber, together with the heat blocking, absorbing, or diverting structure, has been inserted.

19. An arrangement as claimed in claim 1, wherein the target is a urological stone.

\* \* \* \* \*